United States Patent
Miles et al.

(10) Patent No.: US 8,983,567 B1
(45) Date of Patent: Mar. 17, 2015

(54) SYSTEMS AND METHODS FOR VESSEL AVOIDANCE DURING SPINE SURGERY

(75) Inventors: Patrick Miles, San Diego, CA (US); Luiz Pimenta, Sao Paulo (BR)

(73) Assignee: NuVasive, Inc., San Diego, CA (US)

( * ) Notice: Subject to any disclaimer, the term of this patent is extended or adjusted under 35 U.S.C. 154(b) by 518 days.

(21) Appl. No.: 12/848,950

(22) Filed: Aug. 2, 2010

Related U.S. Application Data

(60) Provisional application No. 61/230,696, filed on Aug. 1, 2009.

(51) Int. Cl.
*A61B 17/88* (2006.01)

(52) U.S. Cl.
USPC .......................................................... 600/339

(58) Field of Classification Search
USPC ............. 606/90, 105, 86 A; 623/17.11–17.16
See application file for complete search history.

(56) References Cited

U.S. PATENT DOCUMENTS

| | | | |
|---|---|---|---|
| 6,353,753 B1 | 3/2002 | Flock et al. | |
| 6,516,209 B2 | 2/2003 | Cheng et al. | |
| 6,591,144 B2 | 7/2003 | Pigott | |
| 6,889,075 B2 | 5/2005 | Marchitto et al. | |
| 7,207,949 B2 | 4/2007 | Miles et al. | |
| 7,355,688 B2 * | 4/2008 | Lash et al. | 356/222 |
| 7,442,192 B2 | 10/2008 | Knowlton | |
| 7,749,217 B2 | 7/2010 | Podhajsky | |
| 2003/0236458 A1 | 12/2003 | Hochman | |
| 2006/0217807 A1 * | 9/2006 | Peterman et al. | 623/17.11 |
| 2007/0038126 A1 | 2/2007 | Pyle et al. | |
| 2008/0021331 A1 | 1/2008 | Grinvald et al. | |
| 2008/0249467 A1 | 10/2008 | Burnett et al. | |
| 2008/0294171 A1 * | 11/2008 | Boehm et al. | 606/90 |
| 2009/0149715 A1 | 6/2009 | Mao et al. | |
| 2009/0156916 A1 | 6/2009 | Wang et al. | |
| 2009/0259106 A1 | 10/2009 | Catapano et al. | |
| 2010/0076502 A1 * | 3/2010 | Guyer et al. | 606/86 R |
| 2011/0060229 A1 * | 3/2011 | Hulvershorn et al. | 600/486 |

FOREIGN PATENT DOCUMENTS

| | | |
|---|---|---|
| WO | WO-01-50955 A1 | 7/2001 |
| WO | WO-2007-030331 A1 | 3/2007 |
| WO | WO-2008-124079 A1 | 10/2008 |
| WO | WO-2009-037464 A1 | 3/2009 |
| WO | WO-2010-076808 A1 | 7/2010 |

* cited by examiner

*Primary Examiner* — Christopher Beccia
(74) *Attorney, Agent, or Firm* — Jonathan Spangler; Heather Prado

(57) ABSTRACT

Systems and methods are disclosed for accessing and forming an operative corridor to targeted spinal sites using optical imaging to detect and avoid vascular tissue. The optical imaging may include tissue oximetry to measure the oxygen saturation of tissue proximate to surgical access instruments utilized during surgery. Sensors may be situated near the distal end of the surgical access instruments and monitoring for vessel proximity may be performed during advancement of the instrument.

13 Claims, 4 Drawing Sheets

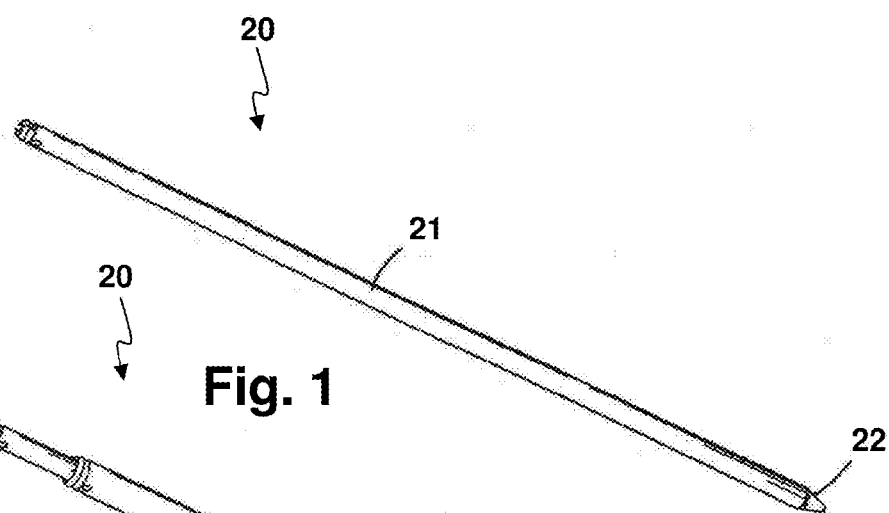
Fig. 1
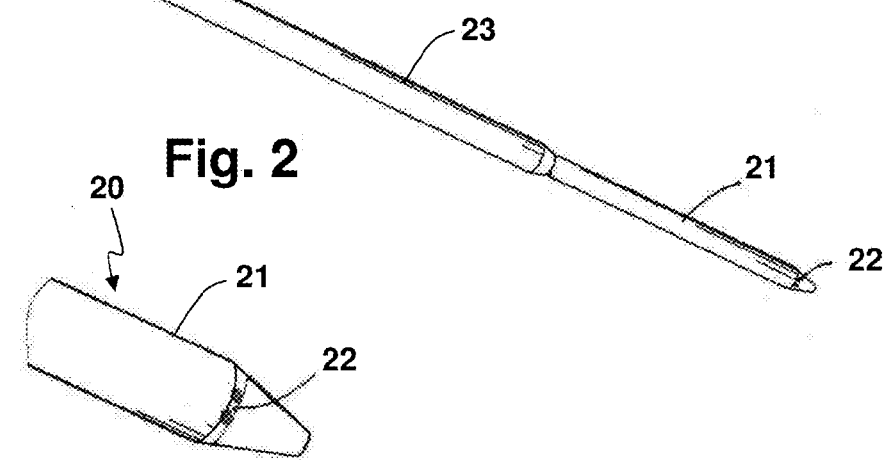
Fig. 2
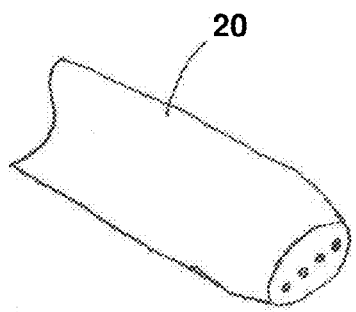
Fig. 3
Fig. 4

SYSTEMS AND METHODS FOR VESSEL AVOIDANCE DURING SPINE SURGERY

CROSS-REFERENCE TO RELATED APPLICATIONS

This application claims the benefit of priority from U.S. Provisional Application No. 61/230,696, filed on Aug. 1, 2009, which is expressly incorporated by reference herein.

FIELD

The present invention relates to spine surgery and more particularly to equipment and methods that aid surgeons in avoiding sensitive tissue when accessing the spine.

BACKGROUND

It has been estimated that between 50 and 70 million people suffer from chronic back pain in the United States. In a significant number of cases, patients who are unaided by conservative therapies choose to undergo spinal surgery. The rate at which caregivers and patients opt for surgery also continues to grow as medical technology advances and surgical options increase. According to some estimates upwards of 750,000 or more spine surgeries are performed in the United States annually.

When necessary, spine surgery may provide great benefit to the patient, often allowing patients to resume activities previously abandoned because of the debilitating pain. Spine surgery, however, is not without risk. Operating on or near the spine means operating in close proximity to the sensitive vascular and neural structures that surround the spine. In particular, when accessing the spinal target site it is important to avoid inadvertently contacting or impinging on these sensitive tissues.

Traditionally, techniques for accessing the lumbar spine have utilized either of a posterior approach (to perform, among other procedures, posterior lumbar interbody fusion (PLIF)) and an anterior approach (to perform, among other procedures, anterior lumbar interbody fusion (ALIF)). Posterior-access is advantageous in that it typically involves traversing a relatively short distance through the patient and is unimpeded by major nerves or vessels. However, posterior-access generally provides limited exposure of the target site (e.g. intervertebral disc), oftentimes having to reduce or cut away part of the posterior bony structures (i.e. lamina, facets, spinous process) to achieve the limited exposure. Anterior-access to the lumbar spine on the other hand provides the advantage of accommodating a relatively large exposure. In order to access the spine from the anterior, however, the surgeon must traverse a greater distance through the patient's body tissue and the various internal organs and vessels located in front of the spine must be moved out of the way, a process that often requires an additional access surgeon.

More recently, techniques for accessing the lumbar spine through a lateral approach have been developed. For example, a minimally invasive retroperitoneal approach which traverses through the psoas muscle and employs neurophysiologic monitoring to detect and avoid nerves which run through the psoas muscle has become a valuable surgical option. The lateral approach may be advantageous in that it accommodates a large exposure akin to an anterior approach yet it may be gained through a smaller incision and without the need to retract the abdominal contents out of the surgical corridor. The lateral approach has proven to be quite successful in a number of ways (e.g. reducing pain, morbidity, recovery time, etc. . . . ). However, depending on patient anatomy, the lateral approach may be impracticable at the L5-S1 (and sometimes L4-L5) level because the iliac crest blocks the disc space. A need therefore still exists for a minimally invasive retroperitoneal approach to the L5-S1 (and sometimes L4-L5) disc space. Regardless of the approach, a need also exists for systems and methods that will allow the surgeon to better detect and avoid vascular tissue near the spine.

SUMMARY OF THE INVENTION

According to a broad aspect, the present application describes a method for accessing a targeted site in a region of the spine through a minimally invasive approach. The method protects the adjacent vascular tissue during access. The method includes the steps of advancing an access instrument through an incision to the targeted spinal site; monitoring for the presence of vascular tissue located in the path of advancement of the access instrument with an optical imaging system that detects vascular tissue; and adjusting the path of advancement when vascular tissue is determined to be located in the path of advancement.

According to a further aspect, the method may be performed wherein the optical imaging system is a tissue oximetry system and monitoring for the presence of vascular tissue includes determining the oxygen saturation levels of tissue adjacent to the surgical access instrument.

According to a further aspect, the distal end of the access instrument includes an array of optical sensors in communication with the optical imaging system. The sensors may include at least one light emitter and at least one photodetector. The access instrument may be a cannulated dilator and the sensors may be arrayed on the sidewalls at the distal end of the dilator. The access instrument may be uncannulated and the sensors may be arrayed on the tip of the distal end.

According to a further aspect, at least one dilator of a sequential dilation system is advanced along the access instrument to the targeted spinal site. The access instrument may be an initial dilator of the sequential dilation system. Monitoring for the presence of vascular tissue located in the path of advancement of each of the sequential dilators of the sequential dilation system may be performed with the optical imaging system. An additional step of advancing a retractor assembly over the outermost of the sequential dilators to the targeted spinal site and expanding the retractor assembly to expand an operative corridor may be performed. An additional step of advancing a k-wire through the initial dilator and anchoring the k-wire within the targeted spinal site prior to advancing the plurality of sequential dilators over the initial dilator may be performed.

According to a further aspect, the minimally invasive approach to the targeted spinal site may be an anterolateral, retroperitoneal approach. The targeted spinal site may be in the lumbosacral region of the spine. The targeted spinal site may be the L5-S1 disc.

According to another broad aspect, the present application describes a method for creating an operative corridor to a spinal target site during spine surgery. The method protects the adjacent vascular tissue during access. The method includes the steps of advancing a surgical access instrument to the surgical target site; detecting the presence of a blood vessel from a sensor situated on the instrument while advancing the instrument; adjusting the path of advancement when the blood vessel is detected; advancing at least one additional instrument along the access instrument to the targeted spinal site; and removing the access instrument to form the operative corridor through the additional instrument.

According to a further aspect, the method may be performed in at least one of cervical, thoracic, lumbar, and sacral regions of the spine. The method may be performed wherein the operative corridor is one of anterior, lateral, anterolateral, posterior, and posterolateral. According to a preferred example, the operative corridor is an anterolateral corridor to the lumbosacral spine.

According to a further aspect, the vessel may be detected by analyzing an optical signal emitted and received by the sensor. The sensor may include at least one photodetector. Detecting the vessel may further comprise sensing the axial position of the vessel relative to the probe. Detecting the vessel may further comprise sensing the radial position of the vessel relative to the probe. According to a further aspect, the step of detecting a vessel is performed by monitoring oxygen saturation.

According to a further aspect, the method may include the additional step of communicating the relative position of the vessel relative to the probe. The communicating may be accomplished by at least one of audio feedback and visual feedback. The visual feedback provided may be at least one of pre-determined alpha-numeric values and pre-determined color categories.

According to another broad aspect, a method for creating a minimally invasive operative corridor to the L5-S1 disc space is described. The method includes the steps of advancing an initial access instrument through an anterolateral retroperitoneal approach to the L5-S1 disc; monitoring for the presence of vascular tissue located in the path of advancement of the initial access instrument with an optical imaging system and adjusting the path of advancement when vascular tissue is determined to be located in the path of advancement; advancing a plurality of sequential dilators of a sequential dilation system over the initial access instrument to the L5-S1 disc; and removing the initial access instrument and all but the outermost dilator of the sequential dilation system to form an operative corridor to the L5-S1 disc space. Alternatively, the additional step of advancing a retractor assembly over the outermost dilator may be performed. The initial access instrument and all the dilators may be removed and the retractor assembly expanded to create the operative corridor to the L5-S1 disc.

According to a further aspect, the initial access instrument is an initial dilator of the sequential dilation system. The additional step of advancing a k-wire through the initial dilator and docking the k-wire within the L5-S1 disc-space prior to advancing the additional dilators of the sequential dilation system over the initial dilator may be performed.

According to another broad aspect, a method of performing spine surgery at L5-S1 vertebral level while protecting adjacent vascular tissue is described. The method includes the steps of (a) advancing a surgical access instrument to the L5-S1 target site; (b) detecting the presence of at least one of the aorta and a common iliac artery from a sensor situated on the instrument while advancing the instrument; and (c) adjusting the path of advancement when the at least one of the aorta and a common iliac artery is detected.

According to a further aspect, the method may be performed to access the L5-S1 space to perform at least one of fusion, nucleus replacement, disc replacement, vertebral body replacement, fixation, stabilization, and discectomy.

According to a further aspect, the vessel may be detected by analyzing an optical signal emitted and received by the sensor. The sensor may include at least one photodetector. Detecting the vessel may further comprise sensing the axial position of the vessel relative to the probe. Detecting the vessel may further comprise sensing the radial position of the vessel relative to the probe. According to a further aspect, the step of detecting a vessel is performed by monitoring oxygen saturation.

According to a further aspect, the method may include the additional step of communicating the relative position of the vessel relative to the probe. The communicating may be accomplished by at least one of audio feedback and visual feedback. The visual feedback provided may be at least one of pre-determined alpha-numeric values and pre-determined color categories.

According to another broad aspect, a method for depositing a spinal implant in the lumbosacral region of the spine is described. The method includes the steps of advancing an initial dilator to targeted site in the lumbsacral region of the spine while monitoring for the presence of vascular tissue proximate to a distal end of the initial dilator with an optical imaging system in communication with sensors situated at the distal end of the dilator; adjusting the advancement path of the dilator as necessary when vascular tissue is detected proximate the distal end; advancing at least one additional dilator of a sequential dilation system over the initial dilator to the targeted site in the lumbosacral spine; removing all the dilators but the outermost dilator of the sequential dilation system to create an operative corridor to the targeted spinal site; advancing one or more instruments through the outermost dilator to prepare the targeted spinal site to receive the spinal implant; and advancing the spinal implant through the operative corridor and into position at the targeted spinal site.

According to a further aspect, the method comprises the additional step of advancing a retractor assembly over the outermost dilator. The sequential dilators may be removed and the retractor assembly expanded to create the operative corridor to the targeted site in the lumbosacral spine.

According to a further aspect, the targeted spinal site in the lumbosacral spine may be one or more of the L5-S1 disc space, the L5 body, the L4-L5 disc space, or the L4 body. The implant may one of a fusion graft, a fusion cage, a nucleus replacement, total disc replacement, and a vertebral body replacement.

According to another broad aspect, a system is described for performing surgery using oxygen saturation monitoring to assess the location of vascular tissue and nerve monitoring to assess the location of nerve tissue. The system includes a control unit having a power supply and a processor programmed to receive user commands, activate light emission in a plurality of predetermined modes, activate electrical stimulation in a plurality of predetermined modes, process signal data according to defined algorithms, display received parameters and processed data, and monitor system status. The system also includes a patient module in communication with the control unit and configured to be positioned within the sterile field of surgery. The patient module includes signal conditioning circuitry and light emission drive circuitry required to perform the light emission and electrical stimulation in the predetermined modes. The patient module includes a processor programmed to perform a plurality of predetermined functions including optical imaging, tissue oximetry, evoked monitoring, and surgical navigation. The system also includes a plurality of surgical accessories adapted to be coupled to at least one of the patient module and control unit to perform the predetermined functions.

According to a further aspect, the control unit includes a display for communicating at least one of alpha-numeric and graphical indicia to a user regarding at least one of the plurality of predetermined functions. The communication may include displaying at least one of alpha-numeric and graphical indicia to the user. The display may be a touch-screen display operable to receive commands from a user.

According to a further aspect the neurophysiologic monitoring involves stimulating the at least one stimulation electrode, sensing a response of a nerve depolarized by the stimulation, determining at least one of nerve proximity and nerve direction based on the sensed response, and communicating the at least one nerve proximity and nerve direction to a surgeon performing the surgery.

According to a further aspect, the system determines the at least one of nerve proximity and nerve direction by determining a stimulation threshold value required to elicit a predetermined neuromuscular response. The system may display at least one of an alpha-numeric character and a color representing the determined threshold. The color may be one of red, yellow, and green. According to a further aspect, the system may determine the stimulation threshold by employing a successive approximation method.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 1 is a is a perspective view of a surgical access instrument equipped with sensors for performing vessel avoidance monitoring in accordance with one example embodiment;

FIG. 2 is a perspective view of the access instrument of FIG. 1 forming part of an access system including sequential dilators, according to one example embodiment;

FIG. 3 is an enlarged view of the distal end of the access instrument of FIG. 1;

FIG. 4 is an enlarged view of the distal end of an access instrument, according to an alternate example embodiment;

DESCRIPTION OF THE PREFERRED EMBODIMENT

Figure 5:
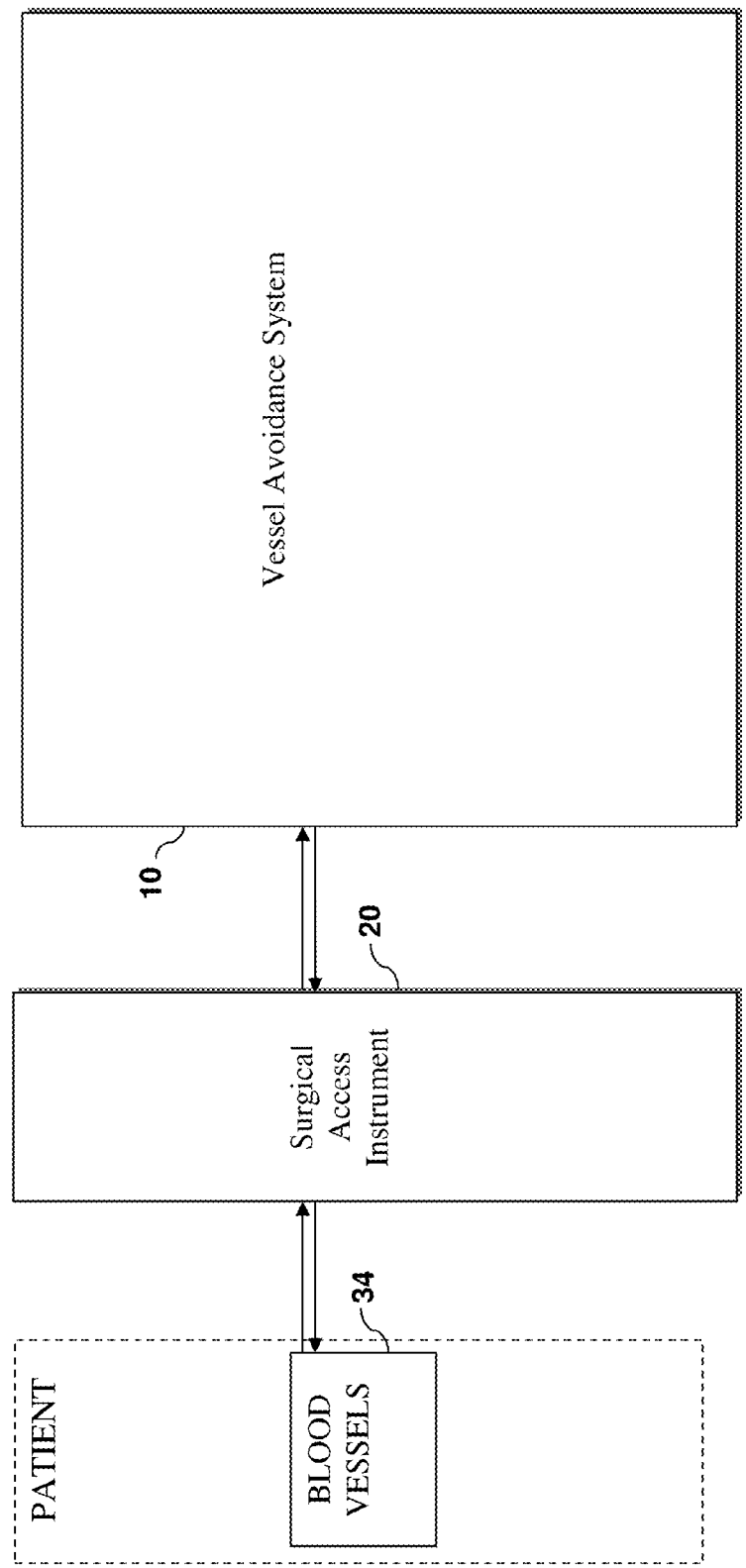
FIG. 5 is a diagram of an exemplary configuration including a vessel avoidance system in accordance with one example embodiment.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and systems disclosed herein boasts a variety of inventive features and components that warrant patent protection, both individually and in combination.

The present application describes accessing a surgical target site in a minimally invasive fashion. To safely access the target site in a minimally invasive fashion, a variety of surgical access instruments may be equipped to perform "vessel avoidance", that is, to scan for and detect the presence of vascular tissue (e.g. veins, arteries) located within or near the path of any of a variety of surgical access instruments used to create an operative corridor to the surgical target site. According to a preferred example, the surgical target site is a portion of the thoracolumbar and/or sacral spine. According to another preferred example, the surgical target site is the intervertebral disc at either of the L5-S1 and L4-5 levels. The surgeon/user then may be alerted as to the presence or absence of a major blood vessel, for example, proximate the surgical access instruments during the creation of an operative corridor. This information can be used to guide the advancement of the surgical access instruments to the surgical target site, facilitating adjustment of the trajectory of their advancement when necessary to avoid vascular tissue. By providing the ability to detect the presence of blood vessels, the visualization required to identify, expose, and avoid the vascular anatomy is minimized.

FIG. 1 illustrates, by way of example, an access instrument 20 equipped with an array of sensors 22 for detecting the presence of vascular tissue. The access instrument 20 may comprise an initial dilator 21 of a sequential dilation system including one or more sequential dilators 23, illustrated in FIG. 2. Though shown only on the initial dilator 21, any of the dilators 23 forming the sequential dilation system may be equipped with the sensors 22. Various other surgical access instruments may be equipped with sensors 22 as well. By way of example only, any of the access instruments shown and described in U.S. Pat. No. 7,207,949, which is expressly incorporated herein by reference, including dilators, retractor blades, shims, and extensions may be equipped with sensors 22 for detecting vascular tissue. As best depicted in FIG. 3, the sensors 22 may be embedded within the walls of the initial dilator 21. The sensors 22 may be exposed at the very tip of the distal end, or close to the distal tip (as shown). The initial dilator 21 is cannulated to allow the optional passage of a k-wire once the dilator has reached the target site. FIG. 4 illustrates an embodiment of another access instrument that is not cannulated. Instead, the sensors 22 are arrayed across the distal end. The sensors 22 include light emitters (e.g. lasers) and photo detectors. According to one example, sensors 22 comprise two light emitters and two photodetectors.

With reference to FIG. 5, by way of example only, the surgical access probe 20, and specifically the sensors 22, may be communicatively linked to a vessel avoidance system 10 capable of carrying out the vascular location assessments mentioned above. The system 10 may comprise any system capable of detecting the presence of vascular tissue. By way of example, the system 10 uses oximetry technology to detect veins (deoxygenated blood) and arteries (oxygenated blood and pulse) by measuring oxygen levels of tissue located near the access probe 20, and particularly by monitoring oxygen saturation. By way of example, the system 10 may utilize technology and methods such as those described in U.S. Pat. No. 6,516,209, PCT Application WO 2007/030331, US Patent Application US 2007/0055119, and/or US Patent Application US 2009/0149715, each of which is expressly incorporated by reference herein. The basic physiologic premise underlying this technology is that near-infrared spectroscopy can be used to measure the oxygen levels of hemoglobin (oxygenated and non-oxygenated), and thus can be utilized to determine when an oximetry probe is approaching vascular tissue. Sensors 22 may be arranged according to any number of configurations, including, but not limited to those discussed in the aforementioned patents.

Figure 6:
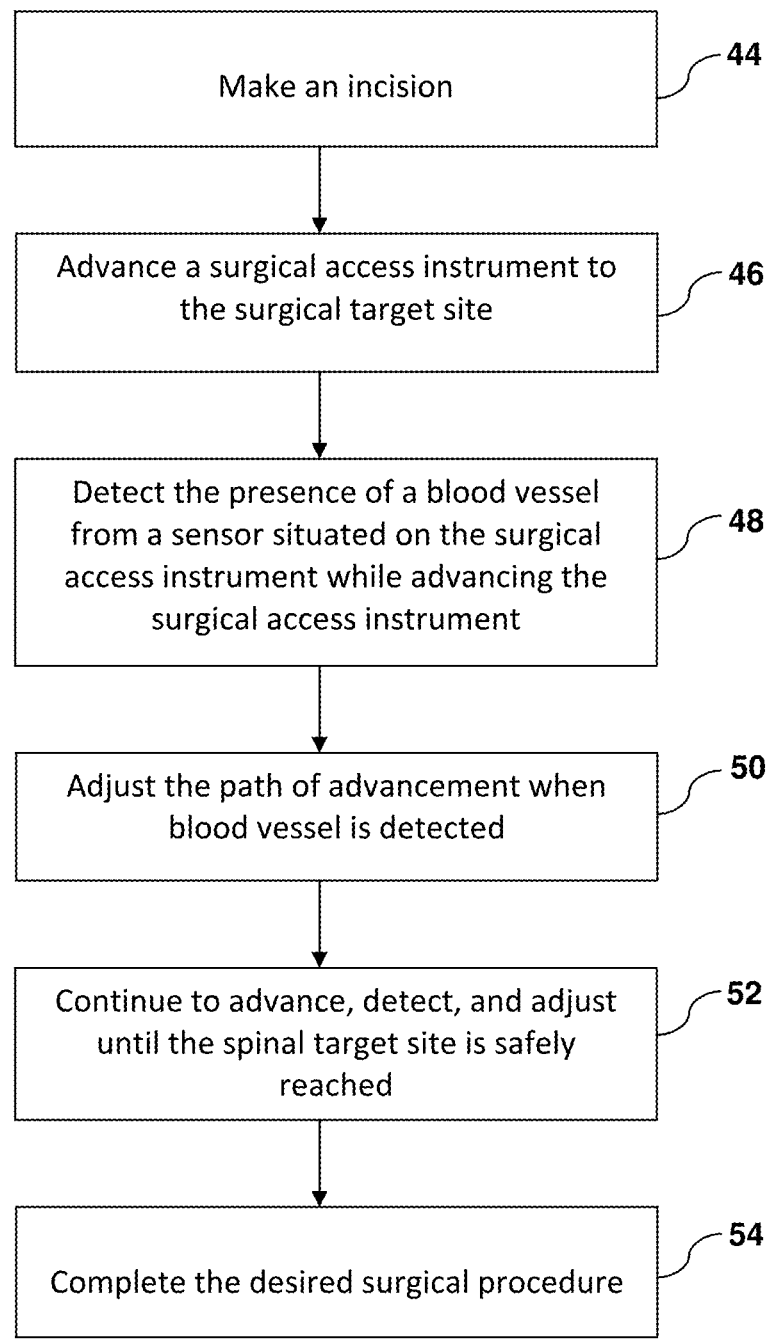
FIG. 6 is a flowchart demonstrating a method of accessing a surgical target site including performance of vessel avoidance, according to one example embodiment.

Turning now to FIG. 6, an exemplary method of accessing a surgical target site in or near the spine of a patient is described utilizing the system 10 or any other system capable of carrying out the steps described. At step 44, an incision is made on the patient's skin. At step 46, a surgical access instrument 20 is advanced to a surgical target site. The surgical target site is for example an intervertebral disc space (e.g. L5-S1 or L4-L5). As the access instrument 20 is advanced to the target site, the system 10 is utilized to detect the presence of a blood vessel 34 proximate to the distal end of the instrument 20 (step 48). The presence of the vessel may be detected by monitoring the oxygen saturation of the tissue proximate the distal end of the instrument 20. When the presence of a blood vessel is detected the path of advancement may be adjusted in order to redirect the instrument away from the vessel (Step 50). When the presence of a vessel is detected any number of mechanisms may be utilized by system 10 to alert the surgeon to the presence of the blood vessel. By way of example only, the system 10 may provide audio alerts, including tones of different frequencies, volumes, duration, or any combination thereof to indicate the relative proximity of the vessel. The system 10 may also utilize visual communication through the use of a display. The visual communication may include any of alphanumeric, graphic, and color indicia, or any combination thereof to indicate the relative proximity. For example, the indication of relative proximity may comprise a numerical display indicating the measured oxygen saturation level, a color from a predetermined color code (e.g. green, yellow, and red, wherein green indicates the access instrument may be safely advanced in the same direction, yellow indicates the access instrument may be advanced with caution, and red indicates that the direction of advancement should be adjusted prior to advancing the access instrument), or a combination thereof. The steps of advancing 46, detecting 48, and adjusting 50, are repeated until the access instrument 20 safely reaches the spinal target site (Step 52). Optionally, steps 46-52 may be repeated for any number of access instruments (e.g. a series of sequential dilators and retractor assembly) until the operative corridor is fully formed. With the operative corridor safely formed, the desired surgical procedure may be completed (step 54). By way of example, the surgical procedure may include one or more of, but is not limited to, fusion, nucleus replacement, total disc replacement, fixation, and stabilization. In accordance with these procedures it will be appreciated that various instruments may be passed through the operative corridor to remove disc material and/or vertebral bone, prepare the space for implantation of an implant (e.g. fusion cage, vertebral body replacement, nucleus replacement, disc replacement), insert an implant into the prepared space, and insert various fixation and/or stabilization implants (e.g. screws, plates, rods, etc. . . . ). Thereafter, all instrumentation is removed from the operative corridor, the surgical access instrument maintaining the operative corridor (e.g. retractor assembly) is removed, and the incision is closed.

Figure 7:
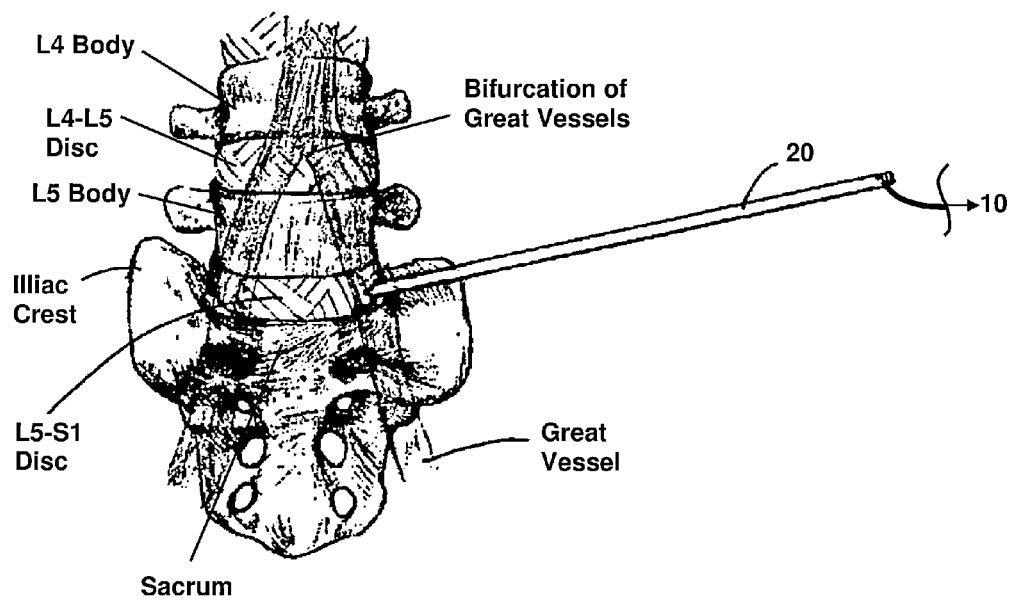
FIG. 7 is an anterior view of the lumbosacral spine showing a preferred anterolateral approach to L5-S1, utilizing the vessel avoidance methods described herein.

In one example, the access instrument 20 and system 10 are utilized to access the L5-S1 intervertebral disc space, as shown in FIG. 7. The preferred approach is an anterolateral approach traversing the retroperitoneal space (obviating the need to retract the abdominal organs out of the way, thus permitting a much smaller incision) to the target site. The great vessels, having bifurcated L5-L5, may be detected and avoided as described, (obviating, or at least reducing, the need to visualize the vessel, again permitting a smaller incision).

The vessel avoidance techniques described above may be performed in conjunction with nerve avoidance monitoring to further facilitate safe access to the spine. The nerve monitoring may be carried out by any number of systems available to detect the presence of a nerve near an instrument. By way of example only, the nerve monitoring system may include that shown and described in PCT Application WO/2008/124079, which is incorporated herein by reference. The nerve monitoring system may be provided as an adjunct to the vessel avoidance system, or alternatively, the vessel avoidance system and the nerve avoidance system may be combined to include the features and functionality of both systems. It is further contemplated that various other applications may also be combined with the nerve monitoring and vessel avoidance features. By way of example, in addition to performing vessel avoidance via oximetry monitoring and nerve avoidance via EMG evoked potential monitoring, the system may utilize ultrasound to supplement either or both of vessel avoidance and nerve avoidance. By way of example, the system may use ultrasound as shown and described in U.S. patent application Ser. No. 11/528,981, which is incorporated herein by reference, to detect the presence of nerves. In similar fashion the ultrasound could be utilized to detect the presence of vessels.

While this invention has been described in terms of a best mode for achieving this invention's objectives, it will be appreciated by those skilled in the art that variations may be accomplished in view of these teachings without deviating from the spirit or scope of the present invention. By way of example the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A method for depositing a spinal implant in the lumbosacral region of the spine, comprising the steps of:
    advancing an initial dilator along an anterolateral path to a targeted site at the anterior column of the lumbosacral region of the spine while monitoring for the presence of vascular tissue proximate to a distal end of the dilator with an optical imaging system in communication with sensors situated at the distal end of the dilator;
    adjusting the advancement path of the dilator as necessary when vascular tissue is detected proximate the distal end;
    advancing at least one additional dilator of a sequential dilation system over the initial dilator to the targeted site in the lumbosacral spine;
    removing all the dilators but the outermost dilator of the sequential dilation system to create an operative corridor to the targeted spinal site;
    advancing one or more instruments through the outermost dilator to prepare the targeted spinal site to receive the spinal implant; and
    advancing the spinal implant through the operative corridor and into position at the targeted spinal site.

2. The method of claim 1, comprising the additional step of advancing a retractor assembly over the outermost dilator, removing all the dilators, and expanding the retractor assembly to create the operative corridor to the targeted spinal site.

3. The method of claim 2, wherein the targeted spinal site is one or more of the L5-S1 disc space, the L5 body, the L4-L5 disc space, or the L4 body.

4. The method of claim 3, wherein the implant is one of a fusion graft, a fusion cage, a nucleus replacement, a total disc replacement, and a vertebral body replacement.

5. The method of claim 1, wherein the optical imaging system is a tissue oximetry system.

6. The method of claim 1, wherein the optical imaging system measures the oxygen saturation levels of tissue proximate the distal end of the initial dilator.

7. The method of claim 1, wherein the distal end of the initial dilator includes an array of optical sensors in communication with the optical imaging system.

8. The method of claim 7, wherein the sensors include a light emitter and a photodetector.

9. The method of claim 8, wherein the distal end includes two light emitters and two photo detectors.

10. The method of claim 7, wherein the initial dilator is cannulated and the sensors are arrayed on the sidewalls at the distal end of the initial dilator.

11. The method of claim 1, comprising the steps of monitoring with the optical imaging system for the presence of vascular tissue located in the path of advancement of the at least one additional dilator of the sequential dilation system while it is advanced over the initial dilator.

12. The method of claim 1, comprising the additional step of advancing a k-wire through the initial dilator and anchoring the k-wire within the targeted spinal site prior to advancing the at least one additional dilator of the sequential dilation system over the intial dilator.

13. The method of claim 1, wherein the path to the targeted site in the lumbosacral region of the spine is an anterolateral, retroperitoneal path.

* * * * *